United States Patent
Pohlmann et al.

(10) Patent No.: US 9,636,470 B2
(45) Date of Patent: May 2, 2017

(54) DEVICE FOR DOSING AND DRY NEBULIZATION

(76) Inventors: Gerhard Pohlmann, Meerbeck (DE); Horst Windt, Burgwedel (DE); Oliver Nolte, Celle (DE); Wolfgang Koch, Steimbke (DE)

( * ) Notice: Subject to any disclaimer, the term of this patent is extended or adjusted under 35 U.S.C. 154(b) by 2121 days.

(21) Appl. No.: 11/887,392

(22) PCT Filed: Apr. 7, 2006

(86) PCT No.: PCT/EP2006/003155
§ 371 (c)(1),
(2), (4) Date: Nov. 8, 2007

(87) PCT Pub. No.: WO2006/108558
PCT Pub. Date: Oct. 19, 2006

(65) Prior Publication Data
US 2009/0000615 A1    Jan. 1, 2009

(30) Foreign Application Priority Data
Apr. 8, 2005  (DE) .................. 10 2005 016 100

(51) Int. Cl.
*A61M 11/02* (2006.01)
*A61M 15/00* (2006.01)
(Continued)

(52) U.S. Cl.
CPC ........ *A61M 11/06* (2013.01); *A61M 15/0065* (2013.01); *A61M 15/0086* (2013.01);
(Continued)

(58) Field of Classification Search
USPC ............ 128/200.14–200.22, 203.12, 203.15, 128/203.16, 203.19, 203.29, 204.26
See application file for complete search history.

(56) References Cited

U.S. PATENT DOCUMENTS 3,442,454 A * 5/1969 Strossner et al. ............. 406/144
6,681,767 B1  1/2004 Patton et al.
(Continued)

FOREIGN PATENT DOCUMENTS

EP     0 561 838 B1   9/1993
FR     2 257 351      8/1975
(Continued)

*Primary Examiner* — Valerie L Woodward
(74) *Attorney, Agent, or Firm* — Nath, Goldberg & Meyer; Jerald L. Meyer; Christopher Thomas

(57) ABSTRACT

The invention relates to a device (1) for dosing and dry nebulization of nebulizable material, comprising a nebulization channel (3), which has a first attachment piece and a second attachment piece, and a source of compressed carrier gas connected to the first attachment piece via a valve for the purpose of sending a carrier gas pressure pulse into the nebulization channel. The device is characterized in that between the first attachment piece and second attachment piece, and above the nebulization channel, a reservoir open only towards the nebulization channel, and used for receiving the nebulizable material, is connected to the nebulization channel such that it is gas-tight with respect to the environment, and that, when the valve is closed, a pressure compensation takes place in the nebulization channel and in the reservoir. The invention also relates to the use of this device for inhaled administration of a powdered pharmaceutical preparation, and to a method for dosing and dry nebulization of nebulizable material by means of such a device.

18 Claims, 5 Drawing Sheets

(51) Int. Cl.
    *A61M 16/14*    (2006.01)
    *A61M 11/06*    (2006.01)
    *B05B 7/14*     (2006.01)
    *A61M 16/20*    (2006.01)
    *A61M 16/00*    (2006.01)

(52) U.S. Cl.
    CPC .......... *A61M 16/14* (2013.01); *A61M 16/202* (2014.02); *B05B 7/1404* (2013.01); *A61M 11/065* (2014.02); *A61M 2016/0027* (2013.01); *A61M 2202/064* (2013.01)

(56) References Cited

U.S. PATENT DOCUMENTS

| | | | |
|---|---|---|---|
| 6,978,779 B2* | 12/2005 | Haveri | 128/200.16 |
| 7,246,617 B1* | 7/2007 | Harmer et al. | 128/203.15 |
| 2002/0158090 A1 | 10/2002 | Odessa | |
| 2004/0254112 A1* | 12/2004 | Hafner | 514/12 |
| 2009/0107491 A1* | 4/2009 | Belson | 128/200.14 |

FOREIGN PATENT DOCUMENTS

| | | |
|---|---|---|
| FR | 2 598 918 A1 | 11/1987 |
| GB | 24848 | 0/1914 |
| GB | 2 310 816 A | 9/1997 |
| WO | 92/10229 A1 | 6/1992 |

\* cited by examiner

DEVICE FOR DOSING AND DRY NEBULIZATION

This application was filed under 35 U.S.C. 371 as a national stage of PCT/EP2006/003155, filed Apr. 7, 2006.

FIELD OF THE INVENTION

The invention relates to a device and a method for dosing and dry nebulization of nebulizable material, in particular powdered pharmaceutical preparations. The invention further relates to the use of such a device for dry nebulization of a powdered pharmaceutical preparation, in particular a lung surfactant preparation.

BACKGROUND OF THE INVENTION

Devices for dry nebulization of nebulizable material are known to the skilled person. In these devices, a nebulizable material, for example a powdered pharmaceutical preparation, is acted upon by a compressed gas or carrier gas in a specially provided chamber and, within this chamber, is converted to a state which is referred to as dry mist. The grains of the material are in this case present in a preferably uniform and finely dispersed form across the entire volume of compressed gas or carrier gas and are then discharged from the chamber in this state via suitable devices.

Such devices are used in particular to form pharmaceutical preparations for inhaled administration to spontaneously ventilating or ventilated patients. For use in spontaneously ventilating patients, the devices are generally connected to a suitable mouthpiece or a breathing mask. In invasive use, i.e. on ventilated patients, these devices are built into the respirator.

In the devices known hitherto for dry nebulization of nebulizable material, however, the problem generally found was that large amounts of pharmaceutical preparations could be delivered to the patient only, if at all, with considerable outlay in terms of equipment, for example using extensive mechanical dosing devices. Generally, the known devices were suitable for the nebulization of pharmaceutical quantities in the range from approximately 1 µg to approximately 20 mg. Pharmaceutical preparations of which large amounts, for example in the gram range, have to be administered to the lungs within a long time period are what are called lung surfactant preparations. Administration of a large amount of such lung surfactants is necessary in acute situations.

In conventional dry nebulizers, a problem generally found was that the nebulizable material, which is present as a loose charge in a storage container, for example a commercially available pharmaceutical vial, tends to agglomerate, by reason of its surface quality and/or its moisture content, resulting in blockage of a comparatively narrow aperture cross section of the vial. Such agglomeration also occurs in lung surfactant preparations. Such blockages can normally be obviated only by suitable mechanical means, in order to ensure a continuous dosing of the nebulizable material over quite a long period of time. In addition, agglomerated particles of nebulizable material, for example lung surfactant preparations, are not generally able to access the lungs.

In emergency treatment of patients in intensive care in particular, it is necessary to ensure rapid and high-dose administration of nebulizable material, in a form accessible to the alveoli, into the lungs with a constant dosage, in rapid sequence and over a period of several minutes. However, in the prior art, such administration was possible, if at all, only with considerable outlay in terms of equipment.

DISCLOSURE OF THE INVENTION

It was therefore an object of the invention to make available a device, its use and a method for dosing and dry nebulization by means of this device, which overcome the disadvantages known from the prior art.

Within the meaning of the present invention, dry nebulization of nebulizable material is understood as its aerosolization, i.e. its conversion into a state carried by carrier gas.

According to the invention, a device is made available in which, in accordance with the principle of a jet pump, a nebulizable material stored in a reservoir is sucked by an underpressure in the reservoir into a nebulization channel and is nebulized in this channel with the compressed gas. The underpressure in the reservoir is in this case generated by the compressed gas flowing past the connection between reservoir and nebulization channel.

The dry nebulizer according to the invention can be used for acute treatment in spontaneously ventilating patients. For this purpose, the second attachment piece of the nebulization channel can be connected via an attachment piece to a device for administration to spontaneously ventilating patients. Examples of such devices are a mouthpiece and breathing mask.

When used on a ventilated patient, i.e. In invasive use, the dry nebulizer is built into the respirator. The second attachment piece of the nebulization channel is in this case preferably joined to the respiratory air intake line of the respirator, in particular to the side port of the respirator.

According to the invention, the duration and/or the time of the pressure pulse from the source of compressed carrier gas is preferably regulated so as to be synchronized, in the case of invasive use, with the respiration rate of the respirator and, in the case of use on spontaneously ventilating patients, with the breathing rate of the patient. According to the invention, a synchronous control is at all times ensured when the mixture of compressed gas and material, that is to say the combination of nebulizable material and compressed carrier gas, reaches the patient before or during an inhalation cycle so that direct uptake of the dry mist by the patient is possible. Of course, the control can also be such that direct uptake of the dry mist by the patient is possible at every x-th breath. The control is such that a control signal is set depending on the length of the nebulization channel and/or of any respirator attachment or attachment piece to a device for administration to spontaneously ventilation patients, and also depending on the desired time of entry of the dry mist into the breathing tube.

Thus, according to the invention, a device is made available in which, during the pressure pulse from the source of compressed carrier gas, i.e. when the valve is opened, an underpressure is present in the reservoir, which underpressure is compensated between the pressure pulses, i.e. when the valve is closed, by gas flowing back. In invasive use of the dry nebulizer according to the invention, the backflowing gas can be a respiratory gas used in the respirator. In the use on spontaneously ventilating patients, it can also be ambient air.

According to the invention, the reservoir is arranged above the nebulization chamber and has a connection to the nebulization channel. This connection is configured so as to be gas-tight with respect to the environment. This connection can consist of one or more openings. By arranging the reservoir above the nebulization channel, the nebulizable material contained in the reservoir collects, as a result of gravity, in the area of the aperture of the reservoir and forms a charge there which, because of the surface quality of the nebulizable material and the choice of a suitable diameter for the aperture(s), prevents the reservoir from emptying into the nebulization channel without output of a pressure pulse. Frictional effects of the particles of the nebulizable material play an important role here. There are no particular restrictions on the connection of the reservoir to the nebulization channel, provided that, when the valve is open to the source of compressed carrier gas, nebulizable material can be sucked into the nebulization channel and the reservoir does not empty into the nebulization channel when the valve is closed.

When the low pressure is applied at the aperture of the reservoir, nebulizable material, on the one hand, but also gas stored in the reservoir, on the other, is sucked into the nebulization channel. As a result, agglomeration of the charge located above the aperture of the reservoir may take place. According to the invention, however, such an agglomeration is broken up by the pressure compensation in the device between the pressure pulses, since ambient air and/or respiratory air flowing back into the nebulization channel also passes through the charge in the reservoir in order to bring about a pressure compensation in the reservoir.

The device according to the invention is designed in such a way that, when the valve is closed, a pressure compensation takes place in the nebulization channel and in the reservoir. This is preferably achieved by the fact that the source of compressed carrier gas is connected to the first attachment of the nebulization channel via a valve in such a way that such pressure compensation is able to take place. According to a preferred embodiment, the pressure compensation is made possible by the fact that the nebulization channel is closed off in a sufficiently gas-fight manner at its first attachment piece. This ensures that the pressure compensation takes place at least for the most part in the nebulization channel and in the reservoir, and not, for instance, via the first attachment piece.

In this way, according to the invention, a uniformly loose charge of the nebulizable material is available after each pressure compensation, as a result of which a step-by-step increasing compaction of the material is avoided and a uniform dosing is guaranteed over a considerable time period. The device according to the invention thus easily allows nebulizable material to be dosed in large amounts in a highly reproducible manner and preferably without mechanical parts. In addition, during the pressure compensation, a loosening of the charge and, if appropriate, a deagglomeration of the nebulizable material is achieved. It is thus possible that the mixture of compressed gas and material predominantly contains particles, preferably exclusively particles, which correspond to the size of the primary particles of the nebulizable material. If the nebulizable material is in the form of powdered pharmaceutical preparations, in particular lung surfactants, it is possible that the primary particles of the pharmaceutical preparation located in the reservoir are present in the mixture of compressed gas and material. To this extent, the device according to the invention permits, preferably completely free of mechanical parts, optimal dispersing of the nebulizable material even down to the size of the primary particles.

The size of the primary particles of the nebulizable material preferably corresponds to a mass median aerodynamic diameter (MMAD) which is such that the particles are able to access the lungs, i.e. the site of action in the alveoli of the lungs. The MMAD of particles that can access the lungs is in the range of 1 to 5 µm. The desired MMAD range, according to the invention, of the particles in the mixture of compressed gas and material is consequently 1 to 5 µm, preferably 1 to 3 µm.

The invention thus provides a device, the use thereof, and a method, by means of which a constant dosing of a nebulizable material is ensured over a considerable time period, and with which large amounts of pharmaceutical preparations of several grams can also be administered to the patient by inhalation over a comparatively short time period, for example of less than 15 minutes.

The device according to the invention thus doses the amount of material to be nebulized preferably solely on the basis of the amount of compressed gas output per pressure pulse and the duration of this pressure pulse. Further mechanical dosing devices are not required in the device according to the invention.

In an advantageous embodiment of the device according to the invention, a dosing chamber is arranged between the reservoir and the nebulization channel. With a suitable choice of the volume and aperture diameter of this dosing chamber toward the nebulization channel, the dosing of an amount of nebulizable material to be output per pressure pulse can advantageously take place without any restrictions concerning the aperture of the reservoir itself toward the dosing chamber. In a particularly advantageous manner, the diameters of the apertures and of the reservoir and also of the dosing chamber lying below this aperture are matched to one another in such a way that exactly the amount of nebulizable material present within the dosing chamber is nebulized during a pressure pulse.

The source of compressed gas in the device according to the invention can be connected to the nebulization channel via a controllable valve. A controllable valve here is particularly preferably a solenoid valve which, in the manner known to the skilled person, controls the time and duration of a pressure pulse into the nebulization channel. The valve is controlled in a manner adapted to the respiration or ventilation rate of the patient, and, in a preferred embodiment of the device according to the invention, a control signal for the valve is emitted by a pressure sensor which, in invasive use, is located inside the respirator.

According to the invention, a pressure compensation takes place between the pressure pulses in the nebulization channel and the reservoir and, if appropriate, the dosing chamber. This pressure compensation can take place by suitable means in the device through the introduction of ambient air. In an advantageous embodiment of the device, however, this pressure compensation takes place through the introduction of respiratory air or ventilation air counter to the direction of the pressure pulse into the nebulization channel and into the reservoir. In this way, in an advantageous manner, a closed and preferably sterile system can be provided in which contamination by microorganisms or pollutants in the ambient air can be safely avoided.

The compressed gas can advantageously be introduced into the nebulization channel via a capillary which particularly preferably has an internal diameter of 0.8 to 1 mm, very preferably of approximately 1 mm. In a particularly advantageous embodiment of the invention, the outlet of the capillary is arranged in the nebulization channel in the area under the connection between reservoir or dosing chamber and the nebulization channel. In this way, a device is made available in which, in an advantageous manner, a swirling of the compressed gas emerging from the capillary supports the swirling of nebulizable material in the nebulization channel and, consequently, the production of a dry mist. This swirling can additionally contribute to breaking up possible agglomerates of the nebulizable material, so that almost exclusively primary particles of the nebulizable material are present in the obtained mixture of compressed gas and material.

The second attachment piece of the nebulization channel of the device according to the invention is advantageously connected to the respirator attachment piece (in the case of invasive use) or to an attachment piece to a device for administration to spontaneously ventilating patients (in the case of non-invasive use) in such a way that the dry mist, i.e. the mixture of compressed gas and material, is transferred to the patient without said mixture striking against baffle surfaces or other obstacles. In such a configuration of the device, the dry mist can pass unimpeded into the ventilation gas of the respirator and can combine with the ventilation gas there. In this way it is possible to prevent a situation where nebulizable material carried by carrier gas strikes obstacles, settles on these and thus is unable to reach the site of action in the lungs. Particularly with a parallel and very particularly concentric arrangement of nebulization channel and preferably the dispersing nozzle to the respirator attachment or the attachment piece to the device for administration to spontaneously ventilating patients, adherence of nebulized material, for example to the inner walls of the respirator attachment (for example the respirator side port or the breathing tube) or of the mouthpiece, is safely suppressed.

In the device according to the invention, 30 to 180 ml of compressed gas can preferably be introduced into the nebulization channel per pressure pulse. In this way it is possible to make available an amount of compressed gas that is particularly advantageous for the nebulization of the desired amount of nebulizable material, and which amount is sufficient to nebulize an amount of nebulizable material which can be taken up by the lungs of the patient in question. At the same time, the amount to be nebulized with such a volume of compressed carrier gas is sufficiently small to exclude the possibility of the patient's breathing or ventilation being adversely affected.

In a further advantageous embodiment of the device according to the invention, a predefined amount of the powdered material, preferably 10 to 50 mg, particularly preferably 10 to 30 mg, can be nebulized per pressure pulse. Thus, a device is made available which in a particularly simple manner permits a uniformly dosed nebulization of powdered material in an amount which is advantageously adapted to the uptake capacity of the lungs of the patient.

The reservoir for the nebulizable material is connected to the device and is preferably a conventional vial for injectable preparations. Its external diameter is typically in the range of 2 cm. Before the vial is fitted on the device according to the invention, its closure piece, usually a rubber stopper, is removed. In a further preferred embodiment of the device according to the invention, the reservoir contains 0.5 to 3 g, particularly preferably 1 to 2 g, of nebulizable material. This means that, in a particularly advantageous manner, the amount of material to be nebulized by the device can be adapted to the dose and duration of administration required particularly in intensive care medicine in inhaled administration of powdered pharmaceutical preparations.

Within the meaning of the application, nebulizable material is understood as a material from which at least some converts into a state carried by carrier gas during operation of the device according to the invention.

The nebulizable material is preferably a pharmaceutical preparation which can be administered in particular by inhalation. This pharmaceutical preparation is advantageously powdered, for example a micronized powder. According to a preferred embodiment, the pharmaceutical preparation comprises a surfactant, in particular a lung surfactant. A lung surfactant is a substance mixture which is contained in the lungs of all vertebrates. It has surface-active properties and reduces the surface tension in the alveolar region of the lungs to such an extent that collapse of the final airway regions is avoided during exhalabon. Essential components in the lung surfactant are proteins, designated by SP-A, SP-B and SP-C. The lung surfactant contained in the nebulizable material is particularly advantageously a recombinant lung surfactant, such as is described in WO 95/32992. This is a mutant of human SP-C (also designated as rSP-C). The most preferred lung surfactant is Venticute® (INN: lusupultide, also designated as rSP-C (FF/l)). rSP-C (FF/l) is described in WO 95/32992. In addition to the described surfactant based on the recombinant surfactant protein C (rSP-C), the pharmaceutical preparation can contain a further lung surfactant from the group of SP-A and SP-B. Moreover, it may also contain phospholipids and other additives familiar to the skilled person.

Particularly preferably, the pharmaceutical preparation is or comprises a powdered lung surfactant preparation which is produced as described in EP-B-877 602. In the process in EP-B-877 602, an organic solution or suspension containing lung surfactant and possibly other constituents is subjected to spray drying. Venticute® is the most preferred lung surfactant in this context.

Accordingly, the nebulization in particular of powdered pharmaceutical preparations containing lung surfactants, in particular Venticute®, is a particularly preferred use of the device.

Lung surfactants are suitable for the prevention and early treatment of acute lung diseases. This use is described in WO 01/76619. Diseases to be treated by lung surfactant are, for example, asthma, pulmonary fibrosis, pneumonias, bronchitis, chronic obstructive pulmonary disease (COPD) and various respiratory distress syndromes (RDS), adult respiratory distress syndrome (ARDS), and infant respiratory distress syndrome (IRDS). The use of the device for nebulization of Venticute® for treatment of ARDS is a particularly preferred area of use.

According to a third aspect of the invention, a method is made available for dosing and dry nebulization of nebulizable material by means of an above-described device. This method includes the steps of introducing a pressure pulse into the nebulization channel, in order to generate an underpressure in the reservoir for the nebulizable material, the resulting sucking of a subsidiary amount of the nebulizable material into the nebulization channel, and the aerosolization of this subsidiary amount inside the nebulization channel. After the mixture of compressed gas and nebulizable material has passed through the dispersing nozzle into the breathing tube or the like, pressure compensation takes place after completion of each pressure pulse in which introduced air from the outside and/or respiratory air flows back from the breathing tube or the like into the nebulization channel and the reservoir.

According to the invention, during this pressure compensation, the gas flows through the charge of material which is located above the aperture of the reservoir and if appropriate above the aperture of the dosing chamber, and which is possibly compacted and agglomerated there, and the latter is thus loosened and deagglomerated.

If, during the preceding pressure pulse, a dosing chamber that may have been used is completely emptied, a charge of material agglomerated above the aperture of the reservoir falls into the dosing chamber and forms a charge above the aperture of the dosing chamber to the nebulization channel. Thus, by particularly simple means, a targeted dosing of the pharmaceutical preparation inside the device is achieved.

In a further preferred embodiment of the method according to the invention, by repeating the steps described above, the content of the reservoir is completely nebulized and delivered to the patient within a defined time period of preferably less than 15 minutes, particularly preferably of less than 10 minutes. In this way, a method is made available which particularly advantageously satisfies the requirements in intensive care of patients or in emergency treatment of patients, where rapid administration of high doses of pharmaceutical preparations is necessary.

BRIEF DESCRIPTION OF THE DRAWINGS

The invention is explained in more detail below by way of example and with reference to FIGS. 1 to 5. The devices shown in the figures simply represent advantageous embodiments of the invention and are not intended to in any way limit the underlying concept of the invention.

In the figures.

EMBODIMENTS OF THE INVENTION

Figure 1:
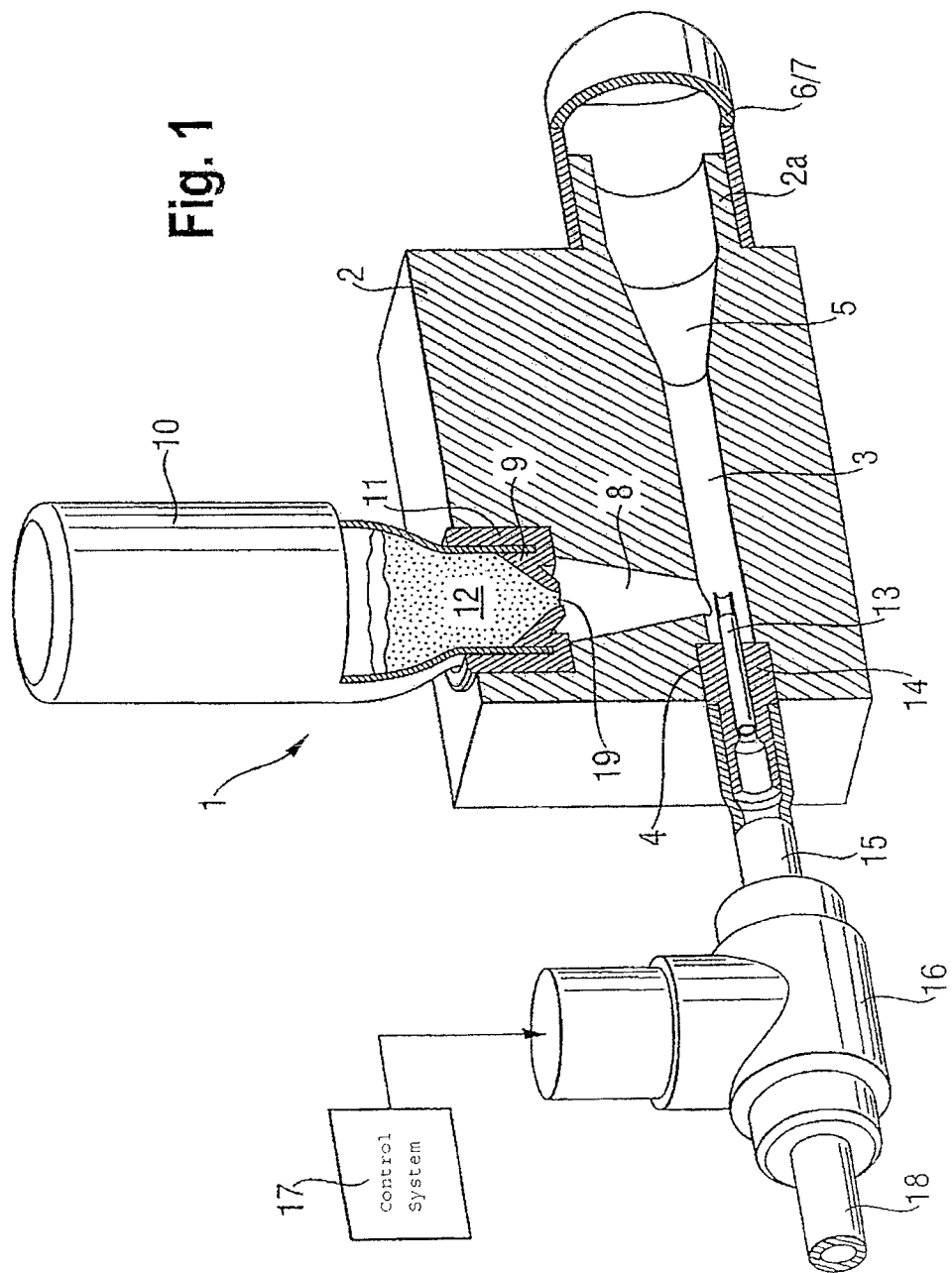
FIG. 1 shows a schematic representation of a first embodiment of the device according to the invention.

In FIG. 1, a partially sectioned, perspective view of the device 1 is shown in which a nebulization channel 3 is arranged inside a nozzle block 2. At its first end (on the left in FIG. 1), the nozzle block 2 comprises a capillary seat 4 into which a capillary tube holder 14 supporting a capillary tube 13 is fitted. This capillary tube holder 14 is in turn connected to a connecting line 15 which opens into a solenoid valve 16, the latter being regulated by a control system labelled schematically with reference number 17. The flow of the compressed gas from the compressed air attachment line 18 into the capillary tube 13 is regulated by the control system 17. At its second end (on the right in FIG. 1), the nebulization channel 3 opens into a dispersing nozzle 5 whose cross section increases continuously in a direction extending away from the capillary tube 13. The dispersing nozzle 5 in turn opens into an attachment piece 2a which is an integral component part of the nozzle block 2 onto which is fitted a respirator attachment piece 6 or an attachment piece 7 to a device for administration to spontaneously ventilating patients. The device 1 also comprises, above the nebulization channel, a receiving seat 9 for the medicament reservoir 10. The edge 11 of the reservoir 10 is fitted into the receiving seat 9 provided in the nozzle block 2, the aperture 19 of the reservoir 10 being located above a dosing chamber 8 with a conically tapering shape. Located above this aperture 19 is a charge of the pharmaceutical preparation 12 which is agglomerated to such an extent that almost no grain of the nebulizable material 12 enters the dosing chamber 8.

Figure 2:
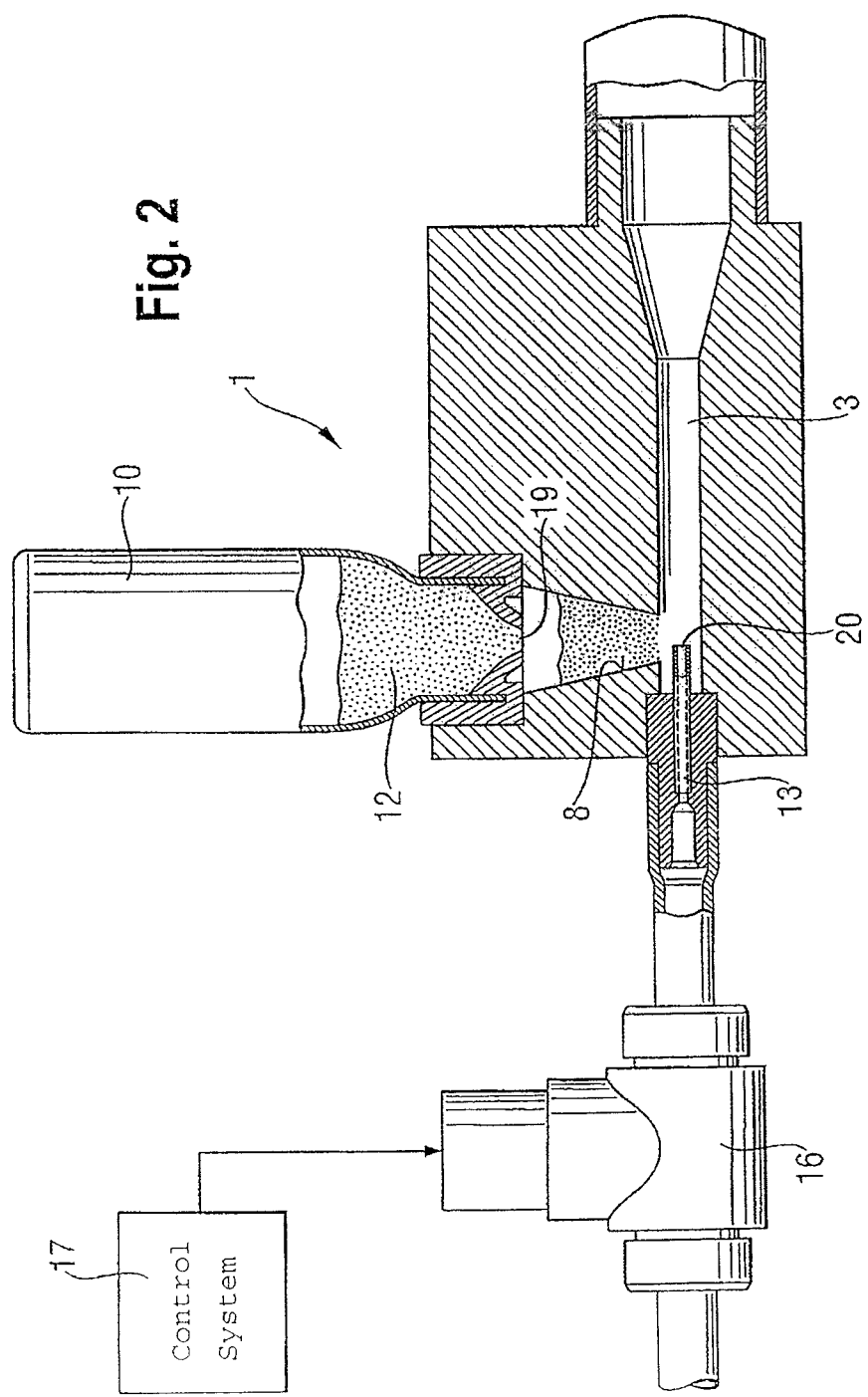
FIG. 2 shows a partially sectioned side view of a first embodiment of the device according to the invention.

FIG. 2 shows a partially sectioned side view of the device 1 shown in FIG. 1, but, in contrast to the view shown in FIG. 1, with the dosing chamber 8 already filled. In this state of the device 1, the dosing chamber 8 has been filled by material falling through the aperture 19 until the material 12 in the reservoir 10 has compacted to the extent that no further material 12 can slip into the dosing chamber 8. At the time shown in FIG. 2, the control system 17 has not emitted any signal to the solenoid valve 16, so that no compressed air passes through the valve 16 and the capillary tube 13 into the nebulization chamber 3.

Figure 3:
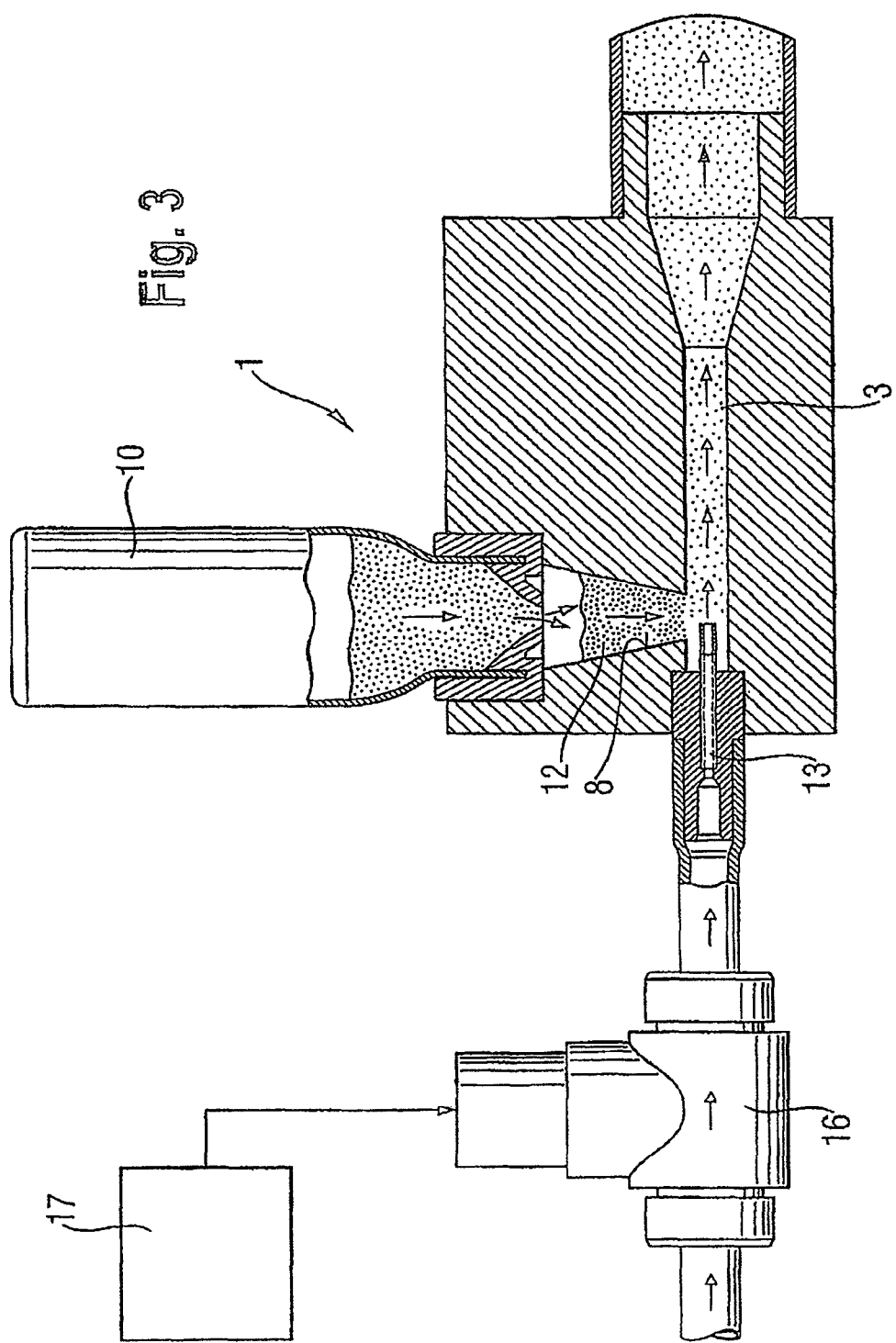
FIG. 3 shows the state of a device according to the invention during output of a pressure pulse into the nebulization chamber.

FIG. 3 shows a partially sectioned side view of the device 1 at a time after the control system 17 has sent an opening signal to the solenoid valve 16. From this time onwards, compressed air passes through the solenoid valve 16 and the capillary tube 13 into the nebulization channel 3. In the nebulization channel 3, an underpressure is created by the flow of the compressed air in the reservoir 10 and in the dosing chamber 8, by means of which underpressure at least the charge of material 12 present in the dosing chamber 8 is entrained in the stream of compressed air, which is indicated by the empty arrows. In the nebulization channel 3, the nebulizable material 12 is aerosolized with the compressed air, such that the dry mist, indicated by the presence of filled arrows and also empty arrows, is guided into the respirator attachment 6 and the attachment piece 7. The dry mist generated in this way can be transported with the respiratory air or ventilation gas into the lungs of the patient.

Figure 4:
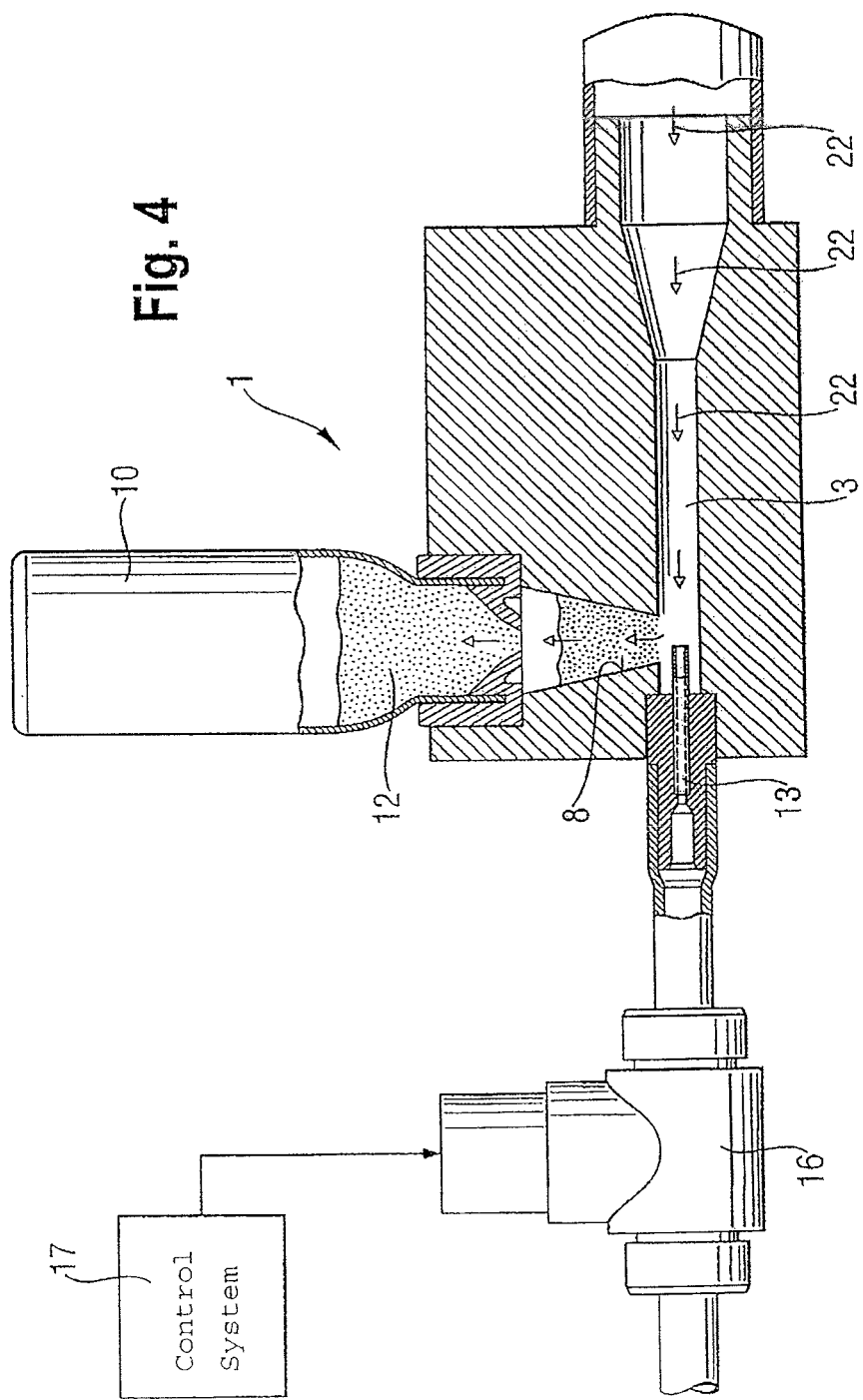
FIG. 4 shows a state of the device according to the invention during a time period between two pressure pulses.

FIG. 4 shows a partially sectioned side view of the first embodiment of the device 1 according to the invention at a time when the control system 17 sends no opening signal to the solenoid valve 16, as a result of which the steam of compressed gas from the compressed-gas source (not shown) into the nebulization channel 3 is also interrupted. On account of the pressure gradient, for example between the respiratory air intake line of the respirator or of the device for administration to spontaneously ventilating patients and of the device 1, ventilation air or respiratory air flows into the nebulization channel 3 and through the dosing chamber 8 into the reservoir 10. By means of the air stream (indicated by the arrows 22) through the respective charges of material in the dosing chamber 8 and the reservoir 10, the charges are loosened and any agglomerations are broken up, so that, after pressure compensation has taken place, nebulizable material 12 that is able to flow is present in the device 1.

Figure 5:
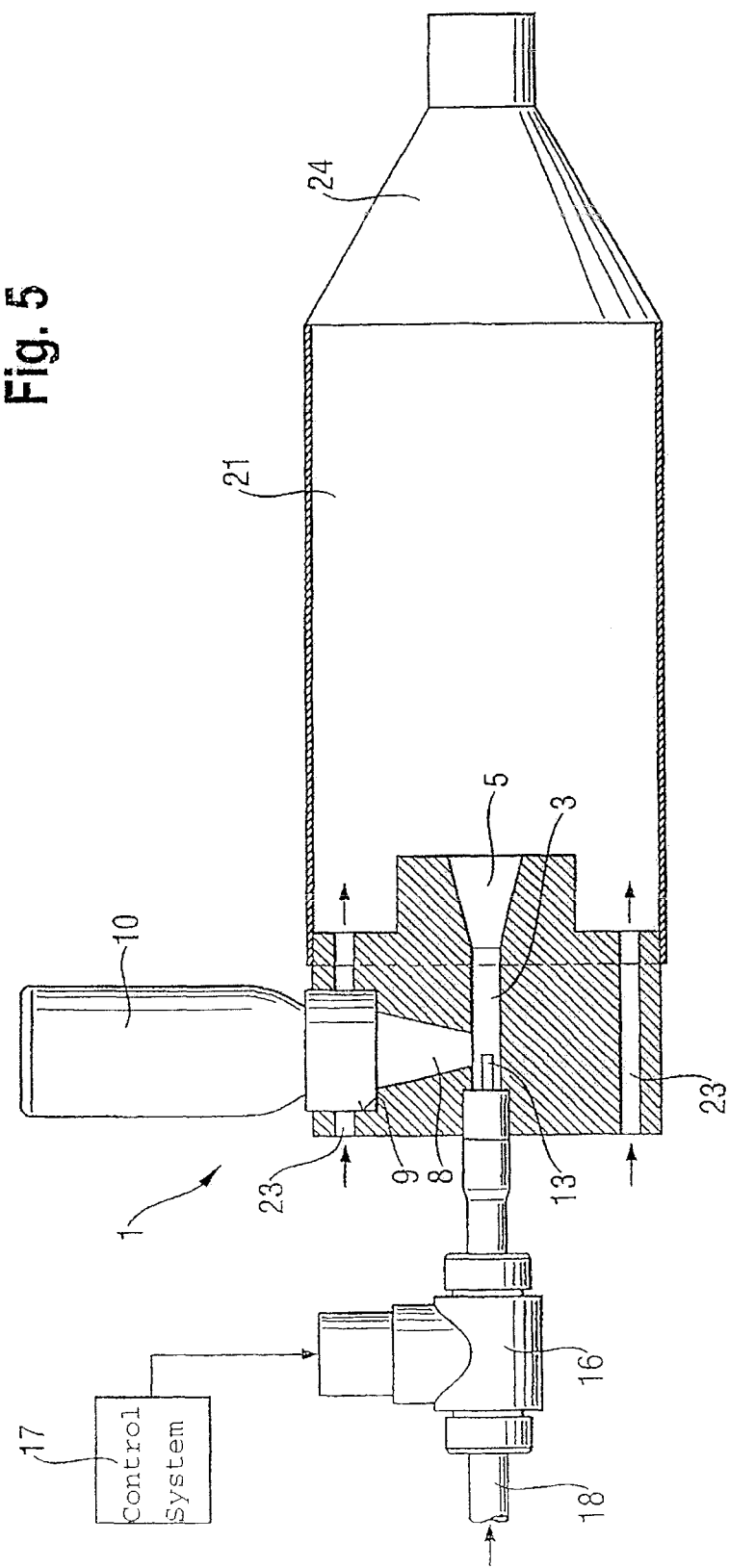
FIG. 5 shows a partially sectioned schematic side view of a second embodiment of the device according to the invention.

FIG. 5 shows an embodiment of the device 1 according to the invention in which the device 1 is arranged concentrically with respect to a cylindrical breathing tube 21. In this embodiment too, compressed gas flows through the compressed air attachment line 18 and the capillary tube 13 into the nebulization channel 3 after the solenoid valve 16 is opened, which solenoid valve 16 is regulated by a control system 17. In this case too, directly above the open end of the capillary tube 13 is the aperture of the dosing chamber 8, above which the reservoir 10 is positioned in a receiving seat 9 provided for it. In this embodiment, the longitudinal axis of the nebulization channel 3 lies on the longitudinal axis of the breathing tube 21 and parallel to a multiplicity of respiratory air intake openings 23 through which respiratory air is conveyed from a source (not shown) through the breathing tube 21. Finally, at its end remote from the device 1, the breathing tube 21 ends in a schematically depicted mouthpiece 24 around which the patient can place his or her lips, so as to inhale the respiratory air to which the dry mist has been added.

The invention claimed is:

1. A device for dosing and dry nebulization of nebulizable material, comprising:
    a nebulization channel connected to a source of compressed carrier gas;
    a valve configured to send a carrier gas pressure pulse into the nebulization channel;
    a reservoir above and open only towards the nebulization channel, the reservoir configured for receiving the nebulizable material and connected to the nebulization channel such that the reservoir is gas-tight with respect to an external environment;
    a conical dosing chamber separate from and connecting to the reservoir; and
    a capillary tube connecting the valve to the nebulization channel, the capillary tube having an outlet in the nebulization channel in an area under the connection between the reservoir and the nebulization channel, wherein
    an inner diameter of the capillary tube is smaller than an inner diameter of the nebulization channel, such that
    upon release of the carrier gas pressure pulse the capillary tube and the nebulization channel form a jet pump flowing the carrier gas past the connection between the reservoir and the nebulization channel and generate an underpressure in the reservoir, and wherein
    when the valve is closed, a pressure compensation takes place by carrier gas flowing back to the reservoir.

2. The device according to claim 1, further comprising a dispersing nozzle connected to the nebulization channel.

3. The device according to claim 1, wherein the valve is a regulated valve.

4. The device according to Claim1, wherein the capillary has an internal diameter of 0.8 to 1 mm.

5. The device according to claim 1, wherein, between pressure pulses, the device is configured to allow respiratory air or ventilation air to flow into the nebulization channel and into the reservoir counter to a direction of the pressure pulse.

6. The device according to claim 1, further comprising a respirator attachment piece connected to the nebulization channel.

7. The device according to claim 6, wherein the valve is configured to synchronize a duration and/or time of the carrier gas pressure pulse with a respiratory rate of a respirator.

8. The device according to claim 6, wherein the nebulization channel concentrically connects to the respirator attachment piece.

9. The device according to claim 1, further comprising a device connected to the nebulization channel and configured for administration to spontaneously ventilating patients.

10. The device according to claim 9, wherein the valve is configured to synchronize a duration and/or time of the pressure pulse with a respiratory rate of a patient breathing in via the device for administration to spontaneously ventilating patients.

11. The device according to claim 1, wherein the nebulization channel is configured such that 30-180 ml of carrier gas can be introduced into the nebulization channel per pressure pulse.

12. The device according to claim 1, wherein the device is configured such that a predefined amount of the nebulizable material can be nebulized per pressure pulse.

13. The device according to claim 1, wherein the reservoir is a vial configured for injectable preparations.

14. The device according to claim 1, wherein the reservoir contains 0.5 to 3 g of nebulizable material.

15. The device according to claim 1, wherein the nebulizable material comprises a pharmaceutical preparation comprising a lung surfactant.

16. The device according to claim 15, wherein the lung surfactant is a surfactant based on recombinant surfactant protein C.

17. The device according to claim 16, wherein the surfactant based on recombinant surfactant protein C is lusupultide.

18. A device for dosing and dry nebulization of nebulizable material, comprising:
    a nebulization channel;
    a reservoir above and open only towards the nebulization channel, the reservoir configured for containing nebulizable material and connected to the nebulization channel such that the reservoir is gas-tight with respect to an environment;
    a capillary tube having a first end and a second end, the first end of the capillary tube having an outlet in an area under the connection between the reservoir and the nebulization channel and the second end of the capillary tube connecting to a valve configured to send a carrier gas pressure pulse through the capillary tube into the nebulization channel; wherein:
    an inner diameter of the capillary tube is smaller than an inner diameter of the nebulization channel, such that
    upon release of the carrier gas pressure pulse the capillary tube and the nebulization channel form a jet pump generating an underpressure in the reservoir by the carrier gas pressure pulse flowing past the connection between the nebulization channel and the reservoir, and
    nebulizable material stored in the reservoir is sucked into the nebulization channel and is nebulized in the channel with the carrier gas pressure pulse, and
    when the valve is closed, a pressure compensation takes place by gas flowing back to the reservoir.

* * * * *

UNITED STATES PATENT AND TRADEMARK OFFICE
CERTIFICATE OF CORRECTION

| | | |
|---|---|---|
| PATENT NO. | : 9,636,470 B2 | Page 1 of 1 |
| APPLICATION NO. | : 11/887392 | |
| DATED | : May 2, 2017 | |
| INVENTOR(S) | : Gerhard Pohlmann et al. | |

It is certified that error appears in the above-identified patent and that said Letters Patent is hereby corrected as shown below:

On the Title Page

Please insert the Applicant as being:

--Fraunhofer-Gesellschaft zur Foerderung der angewandten Forschung e.V.
München, (DE)--

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*